United States Patent [19]

Scherz et al.

[11] Patent Number: 5,656,661
[45] Date of Patent: Aug. 12, 1997

[54] DIHYDROBENZOFURAN AND RELATED COMPOUNDS USEFUL AS ANTI-INFLAMMATORY AGENTS

[75] Inventors: Michael Wiard Scherz, West Chester; Randall Stryker Matthews, Cincinnati, both of Ohio

[73] Assignee: The Procter & Gamble Company, Cincinnati, Ohio

[21] Appl. No.: 481,727

[22] Filed: Jun. 7, 1995

Related U.S. Application Data

[63] Continuation-in-part of Ser. No. 280,892, Jul. 27, 1994, abandoned.
[51] Int. Cl.⁶ .................... A61K 31/34; C07D 307/79
[52] U.S. Cl. .................... 514/469; 514/345; 549/345; 549/462
[58] Field of Search .................... 549/462, 345; 514/462, 469

[56] References Cited

U.S. PATENT DOCUMENTS

| | | | |
|---|---|---|---|
| 3,551,456 | 12/1970 | Bloch et al. | 260/345.2 |
| 4,130,666 | 12/1978 | Moore | 424/331 |
| 4,613,611 | 9/1986 | Floyd, Jr. et al. | 514/443 |
| 4,670,457 | 6/1987 | Doria et al. | 514/470 |
| 4,708,966 | 11/1987 | Loomans et al. | 514/689 |
| 4,849,428 | 7/1989 | Dobson et al. | 549/307 |
| 4,982,006 | 1/1991 | Hudec | 568/322 |

FOREIGN PATENT DOCUMENTS

| | | | |
|---|---|---|---|
| 848 496 | 5/1977 | Belgium . | |
| 0 026 593 | 4/1981 | European Pat. Off. | C07D 307/79 |
| 0 117 675 | 9/1983 | European Pat. Off. | C07D 307/84 |
| 0 113 534 | 7/1984 | European Pat. Off. | C07D 307/83 |
| 0 132 130 | 1/1985 | European Pat. Off. | C07D 307/79 |
| 0 163 537 | 12/1985 | European Pat. Off. | C07D 295/10 |
| 0 286 516 | 10/1988 | European Pat. Off. | C07D 307/92 |
| 0 286 515 | 10/1988 | European Pat. Off. | C07D 307/92 |
| 0 321 432 | 6/1989 | European Pat. Off. | C07C 45/46 |
| 0 322 004 | 6/1989 | European Pat. Off. | C07D 307/79 |
| 0 388 054 | 9/1990 | European Pat. Off. | C07D 207/08 |
| 0 487 071 A1 | 5/1992 | European Pat. Off. | C07D 401/06 |
| 2 370 472 | 11/1976 | France | A61K 31/33 |
| 52-3052 | 1/1977 | Japan | A61K 31/33 |
| 152125d | 11/1977 | Japan . | |
| 53-5178 | 1/1978 | Japan | A61K 31/49 |
| 53-82788 | 7/1978 | Japan | A61K 31/49 |
| 1246 272 | 10/1989 | Japan | A61K 31/34 |
| 3157383 | 7/1991 | Japan | A61K 31/41 |
| 3215485 | 9/1991 | Japan | A61K 31/41 |
| 62-63733 | 1/1993 | Japan | A61K 31/445 |

OTHER PUBLICATIONS

Abeywickrema et. al., J. Org. Chem, 52, pp. 4072-4078 (1987).

J. Herbert Hall et al., "Syntheses and Photophysical Properties of Some 5(2)-Aryl-2(5)-(4-pyridyl)oxazoles and Related Oxadiazoles and Furans", *Journal of Heterocyclic Chemistry*, vol. 29, No. 5, 1992, pp. 1245-1273.

Jye-Shane Yang, et al., "Electrochemical Reduction of Substituted α, α, α–Trifluoroacetophenones. Linear Relationship Between Cyclic Voltammetric Peak Potentials and Hammett Substituent Constants", *Journal of Physical Organic Chemistry*, vol. 3, 1990; pp. 723-731.

v. Dauksas et al., "Syntheses and Pharmalogical activity of 5–substituted Coumarans", *Khim,–Farm. ZH*, vol. 22, No. 3, 1988, pp. 303-307 (non English translation).

V. Dauksas et al., "Synthesis and Antiinflammatory Activity of Acyl–Substituted Benzoxa nd Benzodioxaheterocycles and their Acyclic Analogs", *Khim. Farm. ZH.*, vol. 21, No. 5, 1987, pp. 569-573 (non English translation).

James P. Dunn, et al., "Analgetic and Antiinflammatory 7–Aroylbenzofuran-5–ylacetic Acids and 7–Aroylbenzothiophene-5–ylacetic Acids", *Journal Medical Chemistry*, vol. 29, 1986, pp. 2326-2329.

(List continued on next page.)

Primary Examiner—Bernard Dentz
Attorney, Agent, or Firm—Mary Pat McMahon; Karen F. Clark; Milton B. Graff, IV

[57] ABSTRACT

A compound having the structure:

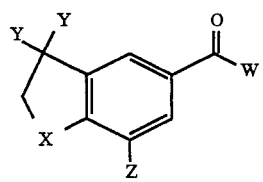

wherein (a) X is oxygen or sulfur;

(b) each Y is independently hydrogen or unsubstituted straight, branched or cyclic alkanyl having from 1 to about 3 carbon atoms,. or the two Y's are bonded to form an alkanyl ring having from 3 to about 7 carbon atoms;

(c) Z is hydrogen or unsubstituted branched or cyclic alkyl, or unsubstituted or alkanyl-substituted phenyl, having from 3 to about 10 atoms other than hydrogen;

(d) W is straight, branched or cyclic alkyl or aryl, unsubstituted or substituted, saturated or mono- or di-unsaturated with double bonds except that no terminal carbon atom of W is part of a double bond; W having from 1 to about 15 atoms other than hydrogen;

pharmaceutical compositions comprising such compounds, and methods of treating inflammation or pain using such compounds.

16 Claims, No Drawings

OTHER PUBLICATIONS

Chakrabarti, J.K., R.J. Eggleton, P.T. Gallagher, J. Harvey, T.A. Hicks, E.A. Kitcen and C. W. Smith, "5–Acyl–3–substituted–benzofuran–2(3H)–ones as Potential Antiinflammatory Agents", *J. Med. Chem.*, vol. 30 (1987), pp. 1663–1668.

Hammond, M.L., I.E. Kopka, R.A. Zambias, C.G. Caldwell, J. Boger, F. Baker, T. Bach, S. Luell and D.E. MacIntyre, "2,3–Dihydro–5–benzofuranols as Antioxidant–based Inhibitors of Leukotriene Biosynthesis", *J. Med. Chem.*, vol. 32 (1989), pp. 1006–1020.

Ortiz de Montelland, P.R. and M.A. Correia, "Suicidal Destruction of Cytochrome P–450 During Oxidative Drug Metabolism", *Ann. Rev. Pharmacol. Toxicol.*, vol. 23 (1983), pp. 481–503.

DIHYDROBENZOFURAN AND RELATED COMPOUNDS USEFUL AS ANTI-INFLAMMATORY AGENTS

This is a continuation-in-part of application Ser. No 08/280,892, filed on Jul. 27, 1994 now abandoned.

TECHNICAL FIELD

The subject invention relates to nonsteroidal anti-inflammatory drugs, particularly to substituted dihydrobenzofuran and related compounds.

BACKGROUND OF THE INVENTION

Certain dihydrobenzofuran compounds and other compounds structurally related thereto have been found to have significant disease altering activities. Such compounds, processes for making them, and uses for them are disclosed in the following references: Doria, Romeo & Corno U.S. Pat. No. 4,670,457 issued on Jun. 2, 1987; Dobson, Loomans, Mathews & Miller U.S. Pat. No. 4,849,428 issued on Jul. 18, 1989; Japanese Patent Publication No. 53-005178 of Yoshitomi Pharm. Ind. KK published Jan. 1, 1978; Hammond, M. L., I. E. Kopka, R. A. Zambias, C. G. Caldwell, J. Boger, F. Baker, T. Bach, S. Luell & D. E. MacIntyre, "2,3-Dihydro-5-benzofuranols as Antioxidant-Based Inhibitors of Leukotriene Biosynthesis", *J. Med. Chem.*, Vol. 32 (1989), pp. 1006–1020; Ortiz de Montellano, P. R & M. A. Correia, "Suicidal Destruction of Cytochrome P-450 during Oxidative Drug Metabolism", *Ann. Rev. Pharmacol. Toxicol.*, Vol. 23 (1983), pp. 481–503; Chakrabarti, J. K., R. J. Eggleton, P. T. Gallagher, J. Harvey, T. A. Hicks, E. A. Kitchen, and C. W. Smith, "5-Acyl-3-substituted-benzofuran-2(3H)-ones as Potential Anti-inflammatory Agents", *J. Med. Chem.*, Vol. 30 (1987), pp. 1663–1668.

It is an object of the subject invention to provide compounds which have effective anti-inflammatory and/or analgesic activity.

It is a further object of the subject invention to provide such compounds which cause few adverse side effects.

It is also an object of the subject invention to provide methods for treating inflammation and/or pain using the subject compounds.

SUMMARY OF THE INVENTION

The subject invention compounds having the structure:

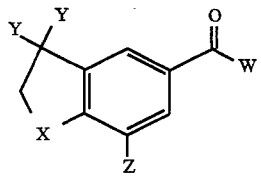

wherein
(a) X is oxygen or sulfur;
(b) each Y is independently hydrogen or unsubstituted straight, branched or cyclic alkanyl having from 1 to about 3 carbon atoms, or the two Y's are bonded to form an alkanyl ring having from 3 to about 7 carbon atoms;
(c) Z is hydrogen or unsubstituted branched or cyclic alkyl, or unsubstituted or alkanyl-substituted phenyl, having from 3 to about 10 atoms other than hydrogen;
(d) W is straight, branched or cyclic alkyl or aryl, unsubstituted or substituted, saturated or mono- or di-unsaturated with double bonds except that no terminal carbon atom of W is part of a double bond; W having from 1 to about 15 atoms other than hydrogen

DETAILED DESCRIPTION OF THE INVENTION

As used herein, unless otherwise indicated, "alkyl" means a straight, branched or cyclic hydrocarbon chain, saturated or unsaturated, unsubstituted or substituted. Preferred alkyl are straight chain. Preferred branched alkyl have one or two branches, preferably one branch. Preferred cyclic alkyl are monocyclic or are straight chain and monocyclic combination, especially a straight chain with a monocyclic terminus. Preferred alkyl are saturated. Unsaturated alkyl have one or more double bonds or/and one or more triple bonds. Preferred unsaturated alkyl have one or two double bonds or one triple bond, more preferably one double bond. Preferred alkyl are unsubstituted. Preferred substituted alkyl are mono-, di-, or trisubstituted, more preferably monosubstituted. Preferred alkyl substituents include halo, hydroxy, oxo, alkoxy (e.g., methoxy, ethoxy, propoxy, butoxy, penfoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), aryl (e.g., phenyl, tolyl, alkyloxphenyl, alkyloxycarbonylphenyl, halophenyl), heterocyclyl, heteroaryl, amino (e.g., amino, mono- and di-$C_1$–$C_3$ alkanylamino, methylphenylamino, methylbenzylamino, $C_1$–$C_3$ alkanylamido, carbamamido, ureido, guanidino). Preferred alkyls also include alkyls having heteroatoms within the chain said heteroatoms selected from the group consisting of oxygen, sulfur, nitrogen and combinations thereof.

As used herein, "alkanyl" means a saturated alkyl.

As used herein, "alkoxy" means —O-alkyl.

As used herein, "terminal carbon atom" means a carbon atom in an alkyl chain which is bonded to only one non-hydrogen atom; "non-terminal carbon atom" means a carbon atom in an alkyl chain bonded to two or more non-hydrogen atoms.

As used herein, "aryl" means a moiety having an unsubstituted or substituted aromatic ring having 6 to about 10 carbon atoms. Preferred aryl are phenyl and naphthyl; most preferred aryl is phenyl. Preferred aryl are unsubstituted. Preferred substituted aryl are mono-, di-, or trisubstituted, more preferably monosubstituted. Preferred aryl substituents include alkyl, alkoxy, hydroxy, thiol, amino, halo. Preferred alkyl substituents are methyl, ethyl and propyl.

As used herein, "heterocyclyl" means a moiety having a saturated or unsaturated non-aromatic ring having from 3 to about 8 ring atoms, including from 2 to about 6 carbon atoms and from 1 to about 4 heteroatoms selected from O, S, and N. Preferred heterocycles are saturated. Preferred heterocycles have 5 or 6 atoms in the ring including 1 or 2 heteroatoms in the ring, also preferably 1 heteroatom in the ring. Specific preferred heterocycles include piperidinyl, tetrahydrothienyl, pyrrolidinyl, piperazinyl, morpholinyl, tetrahydropyranyl, tetrahydrofuranyl, imidazolidinyl, pyrazolidinyl, oxazolidinyl, isoxazolidinyl, oxathiazolidinyl, isothiazolidinyl, azepinyl, oxepinyl, triazolidinyl. Heterocycles are unsubstituted or substituted, preferably unsubstituted. Preferred substituted heterocycles are mono-, di-, or trisubstitued, more preferably monosubstituted. Preferred heterocycle substitutents include alkyl, halo, hydroxy, alkoxy, thio, amino, amido, ureido, guanidino, thiocarbamamido, thioureido.

As used herein, "heteroaryl" means a moiety having an aromatic ring having 5 or 6 ring atoms including from 2 to 5 carbon atoms and from 1 to 3 heteroatoms selected from O, S and N. Preferred heteroaryls have 1 or 2 heteroatoms in the ring, also preferably 1 heteroatom in the ring. Specific preferred heteroaryls include pyrrolyl, imidazolyl, pyridyl, pyrimidinyl, pyrazinyl, oxazolyl, isoxazolyl, pyranyl, thienyl, tetrazolyl, thiazolyl, isothiazolyl, furyl, oxathiazolyl. Heteroaryls are unsubstituted or substituted, preferably unsubstituted. Preferred substituted heterocycles are mono-, di-, or trisubstituted, more preferably monosubstituted. Preferred heteroaryl substituents include alkyl, halo, hydroxy, alkoxy, thio, amino, amido, ureido, guanidino, thiocarbamamido, thiouredio.

As used herein, "halo" means fluoro, chloro, bromo or iodo. Preferred halo are fluoro, chloro and bromo; more preferred are chloro and bromo, especially chloro.

The subject invention involves compounds having the following structure:

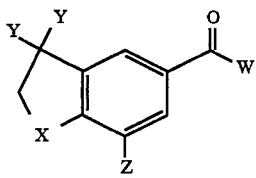

In the above structure, X is O or S. Preferred X is O.

In the above structure, each Y is independently selected from hydrogen, or unsubstituted straight, branched or cyclic alkanyl having from 1 to about 3 carbon atoms, or the Y's are bonded together to form a cyclic alkanyl ring having from 3 to about 7 carbon atoms in the ring. Each Y is preferably hydrogen, methyl, ethyl or cyclopropyl; more preferably hydrogen or methyl; most preferably methyl. When the Y's are bonded together to form a cyclic ring, the ring is preferably cyclopropyl, cyclobutyl or cyclopentyl, more preferably cyclopropyl.

In the above structure, Z is selected from the group consisting of hydrogen, unsubstituted branched or cyclic alkyl, and unsubstituted or alkanyl-substituted phenyl, having from 3 to about 10 atoms other than hydrogen. Z is preferably branched alkanyl having from about 4 to about 8 carbon atoms, more preferably from about 4 to about 6 carbon atoms. Z is preferably branched alkanyl having 2 or more branches, more preferably 2 branches. Preferred branched alkanyl Z include t-butyl, isopropyl, neopentyl; most preferred is t-butyl. Preferred cyclic alkanyl Z include cyclopropyl, cyclobutyl, cyclopentyl, cyclohexyl, cycloheptyl; most preferred is cyclopentyl. Also preferred Z is unsubstituted phenyl or phenyl substituted with methyl.

In the above structure, W is straight, branched or cyclic alkyl or aryl, unsubstituted or substituted, saturated or mono- or di-unsaturated with double bonds except that no terminal carbon atom of W is part of a double bond; W having from 1 to about 15 atoms other than hydrogen. Preferred W have from about 2 to about 9 atoms other than hydrogen; more preferred W have from about 3 to about 7 atoms other than hydrogen. Preferred substitutents for alkyl W include hydroxy, thiol, amino, halo, phenyl, heterocycle and heteroaryl; more preferred include hydroxy, thiol, halo, and saturated heterocycle; more preferred still are hydroxy and chloro.

Preferred straight chain alkyl W are alkanyl, including methyl, ethyl, n-propyl and n-butyl. Preferred straight chain alkanyl W are unsubstituted or substituted; if substituted, they are preferably monosubstituted with hydroxy or halo, especially chloro.

Preferred branched chain alkyl W are alkanyl, preferably having a single alkanyl branch, more preferably a single methyl branch. Preferred branched chain alkanyl W are unsubstituted or substituted; if substituted, they are preferably monosubstituted with hydroxy or halo, especially chloro.

Preferred cyclic alkyl W are alkanyl, preferably cyclopropyl, cyclobutyl or cyclopentyl, or $C_1$ to about $C_4$ straight chain alkanyl with a terminal cyclopropyl, cyclobutyl or cyclopentyl, preferably cyclopropyl. Preferred cyclic alkanyl W are unsubstituted.

Preferred unsaturated alkyl W have one double bond between non-terminal carbon atoms, the double bond preferably being between the carbon atom bonded to the carbonyl carbon atom and an adjacent non-terminal carbon atom. Preferred unsaturated alkyl W are unsubstituted. Preferred unsaturated alkyl W are straight chain or branched chain with a single branch, preferably a single methyl branch.

Preferred cyclic aryl W are phenyl or naphthyl, preferably phenyl. Preferred cyclic aryl W are unsubstituted.

Preferred compounds of the subject invention include those having the above structure with the X, W, the two Y's, and Z as indicated in the following table:

| Compound No. | X | W | Y | Z |
|---|---|---|---|---|
| 1 | O | methyl | methyl, methyl | t-butyl |
| 2 | O | ethyl | methyl, methyl | t-butyl |
| 3 | O | n-propyl | methyl, methyl | t-butyi |
| 4 | O | n-butyl | methyl, methyl | t-butyl |
| 5 | O | i-propyl | methyl, methyl | t-butyl |
| 6 | O | cyclopropyl | methyl, methyl | t-butyl |
| 7 | O | cyclopentyl | methyl, methyl | t-butyl |
| 8 | O | 3-cyclopropylpropyl | methyl, methyl | t-butyl |
| 9 | O | 2-chloro-2-methylpropyl | methyl, methyl | t-butyl |
| 10 | O | 2-hydroxy-2-methylpropyl | methyl, methyl | t-butyl |
| 11 | O | 2-methyl-1-propenyl | methyl, methyl | t-butyl |
| 12 | O | 2-methylcyclopropyl | methyl, methyl | t-butyl |
| 13 | O | 2-thio-2-methylpropyl | methyl, methyl | t-butyl |
| 14 | O | methyl-1-hydroxycyclopentyl | methyl, methyl | t-butyl |
| 15 | O | 3-cyclopropylpropyl | methyl, methyl | cyclopentyl |
| 16 | O | 2-methyl-1-propenyl | H, H | t-butyl |
| 17 | O | methylthiomethyl | methyl, methyl | t-butyl |
| 18 | O | n-butyl | H, H | t-butyl |
| 19 | O | 3-cyclopropylpropyl | H, H | t-butyl |
| 20 | O | n-pentyl | methyl, methyl | t-butyl |
| 21 | O | n-butyl | methyl, methyl | cyclopentyl |
| 22 | O | 1-methylethyl | H, H | t-butyl |
| 23 | O | ethyl | H, H | t-butyl |
| 24 | O | methyl | H, H | t-butyl |
| 25 | O | 2-hydroxy-2-methylpropyl | H, H | t-butyl |
| 26 | S | n-propyl | methyl, methyl | t-butyl |
| 27 | S | n-butyl | methyl, methyl | t-butyl |
| 28 | O | phenyl | methyl, methyl | t-butyl |
| 29 | O | 3-cyclopropylpropyl | methyl, methyl | H |
| 30 | O | 2-hydroxy-2-methylpropyl | methyl, methyl | H |
| 31 | O | methylsulfinylmethyl | methyl, methyl | t-butyl |
| 32 | O | acetylthiomethyl | methyl, methyl | t-butyl |
| 33 | O | ethylthiomethyl | methyl, methyl | t-butyl |

In order to determine and assess pharmacological activity, testing of the subject compounds in animals is carried out using various assays known to those skilled in the art. The anti-inflammatory activity of the subject compounds can be conveniently demonstrated using an assay designed to test the ability of the subject compounds to antagonize the local edema which is characteristic of the inflammatory response. Examples of such known tests include the rat carrageenan edema test, the oxazolone-induced inflamed mouse ear test, and the mouse arachadonic acid-induced inflamed ear test. Analgesic activity may be tested in art-known models such as the phenylbenzoquinone-induced writhing test in mice, and the Randall & Selitto test in rats. Another useful art-known test is the rat adjuvant arthritis test which is a useful model for assessing anti-inflammatory activity, anti-arthritic and anti-resorptive activity in a chronic, rather than an acute, model.

These and other appropriate tests for pharmacological activity are disclosed and/or referred to in Moore U.S. Pat. No. 4,130,666 issued on Dec. 19, 1978; Katusmi, et al. U.S. Pat. No. 4,431,656 issued Feb.14, 1984; Katsumi, et al. U.S. Pat. No. 4,440,784 issued on Apr. 3, 1984; Japanese Patent Application 85/54315 of Katsumi, et al., published Mar. 28, 1985; European Patent Application No. 0,059,090 of Yamanuchi Pharmaceutical Company Ltd., published Sep. 1, 1982; Opas, E. V., R. J. Bonney & J. L. Humes, "Prostaglandin and Leukotriene Synthesis in Mouse Ears Inflamed by Arachadonic Acid", *The Journal of Investigative Dermatology*, Vol. 84, No. 4 (1985), pp. 253–256; Swingle, K. F., R. L. Bell & G. G. I. Moore, "Anti-inflammatory Activity of Antioxidants", *Anti-inflammatory and Antirheumatic Drugs*, Vol. III, Chapter 4, K. D. Rainsford, ed., CRC Press, Inc., (1985), pp. 105–126; Adamkiewicz, V. W., W. B. Rice & J. D. McColl, "Antiphlogistic Effect of Trypsin in Normal and in Adrenalectomized Rats", *Canadian Journal of Biochemistry & Physiology*, Vol. 33 (1955), pp. 332–339; Sellye, H., "Further Studies Concerning the Participation of the Adrenal Cortex in the Pathogenesis of Arthritis", *British Medical Journal*, Vol. 2 (1949), pp. 1129–1135; and Winter, C. A., E. A. Risley & G. W. Nuss, "Carrageenan-Induced Edema in Hind Paw of the Rats as an Assay for Antiinflammatory Drugs" *Proceedings of Society of Experimental Biology and Medicine*, Vol. 111 (1962), pp. 544–547; Otterness, I., & M. L. Bliven, "Laboratory Methods for Testing Nonsteroidal Antiinflammatory Drugs", *Nonsteroidal Antiinflammatory Drugs*, Chapter 3, J. G. Lombardino, ed., John Wiley & Sons, Inc. (1985), pp. 111–252. Hitchens, J. T., S. Goldstein, L. Shemano & J. M. Beiler, "Analgesic Effects of Irritants in Three Models of Experimentally-Induced Pain", *Arch. Int. Pharmacodyn.*, Vol. 169, No. 2 (1967) pp. 384–393; Milne, G. M. & T. M. Twomey, "The Analgetic Properties of Piroxicam in Animals and Correlation with Experimentally Determined Plasma Levels", *Agents and Actions*, Vol. 10, No. 1/2 (1980), pp. 31–37; Randall, L. O. & J. J. Selitto, "A Method for Measurement of Analgesic Activity on Inflamed Tissue", *Arch. Int. Pharmacodyn.*, Vol. 111, No. 4 (1957), pp. 409–419; Winter, C. A. & L. Faltaker, "Nociceptive Thresholds as Affected by Parenteral Administration of Irritants and of Various Antinociceptive Drugs", *J. Pharmacol. Exp. Ther.*, Vol. 148, No. 3 (1965), pp. 373–379; the disclosure of all these references are incorporated herein by reference.

Many anti-inflammatory drugs, particularly non-steroidal anti-inflammatory drugs (NSAIDs) cause undesirable gastrointestinal side effects, especially when dosed perorally; such side effects may include ulcers and erosions. These side effects, which are often asymptomatic, can become serious enough to require hospitalization and can even be lethal. Compounds of the subject invention generally cause fewer such gastrointestinal side effects compared to other NSAIDs. Some compounds of the subject invention are even gastroprotective, protecting the stomach and intestines from ulcers and erosions, particularly those caused by ethanol or other NSAIDs.

Certain NSAIDs, when dosed systematically, cause an undesirable increase in systemic levels of certain liver enzymes. Compounds of the subject invention generally cause little or no liver enzyme side effects.

Compounds useful in the subject invention can be made using the following general reaction scheme:

Scheme 1

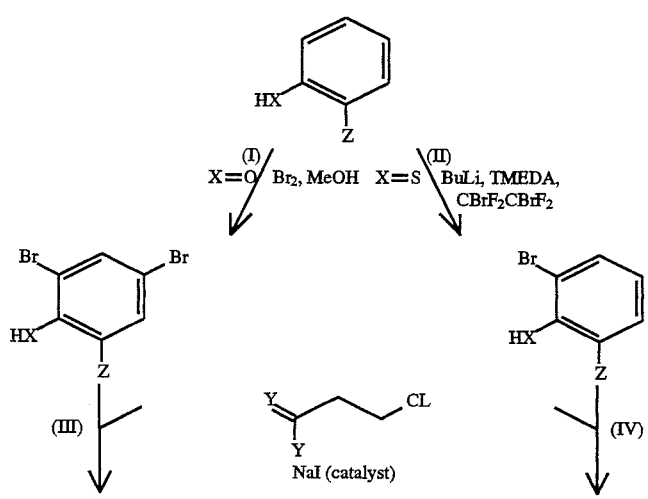

-continued
Scheme 1

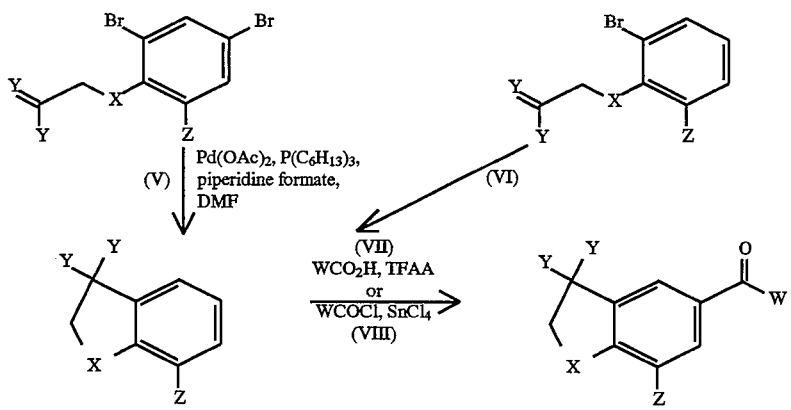

In Scheme 1, X, Y, Z and W are as defined above. The substituted phenols or thiophenols depicted as starting materials in Scheme 1 are either known, commercially available, or readily prepared by methods known to one of ordinary skill in the art. Bromination of such phenol or thiophenol starting materials can be carried out as depicted in steps (I) and (II) in Scheme 1. For example, 2,4-dibromo-6-t-butylphenol is obtained by reaction of 2-t-butylphenol with bromine in MeOH. 2-Bromo-6-t-butylthiophenol is obtained by treatment of 2-t-butylthiophenol with excess alkyl lithium reagent in a strongly coordinating solvent such as tetramethylethylenediamine (TMEDA) or hexamethylphosporamide followed by reaction with 1,2-dibromo-tetrafluoroethane in an ethereal solvent at low temperature.

Allylation of such brominated substituted phenol or thiophenol with an allylic halide is depicted in steps (111) and (IV) of Scheme 1. Allylic halides such as 3-chloro-2-methylpropene, 1-chloro-2-methyl-2-butene, 1-chloromethylcylcopentene, or 1-chloromethylcyclobutene are reacted with appropriate brominated substituted phenols and thiophenols using reaction conditions readily apparent to a skilled organic chemist. For example, 3-chloro-2-methylpropene in the presence of catalytic sodium iodide in refluxing acetone reacts with substituted phenols or thiophenols to provide the corresponding allylated compounds.

Such allylated compounds are cyclized as depicted in steps (V) and (VI) of Scheme 1. Reaction conditions useful for achieving this cyclization are known to those skilled in the art, and can, for example, involve either the intermediacy of free radical species, or Pd or Ni coordination complexes. One method of achieving the ring closure is in hot dimethylformamide solvent with $Pd^{2+}$ or $Ni^{2+}$ salts in the presence of trivalent alkyl or aryl phosphorous compounds, such as tricyclohexylphosphine ($P(C_6H_{13})_3$), triphenylphosphine or analogous materials. An alternative method when Z has no hydrogen bonded to its alpha-carbon atom (the carbon bonded to the phenyl ring), involves treatment of the allylated compound with a reductant such as tri-n-butyltinhydride, tetra-kis-trimethylsilylsilane, or hypophosphorus acid in hot dioxane, in the presence of a base (such as triethylamine, diisopropyethylamine, or the like) and a radical chain initiator such as azo-bis-isobutyrylnitrile.

Compounds of the subject invention are prepared from the fused-ring compounds provided by steps (V) and (VI) of Scheme 1 by one of several methods. Acylation of such fused-ring compounds with an appropriate carboxylic acid as depicted in Step (VII) of Scheme 1 can be achieved under reaction conditions readily apparent to one skilled in the art. For example, this reaction can be performed in an inert halogenated solvent, such as $CH_2Cl_2$ using an activating agent such as trifluoroacetic acid anhydride at the appropriate temperature. Alternatively, the same transformation can be accomplished as depicted in Step (VIII) of Scheme 1 using an acid chloride, derived from the appropriate organic carboxylic acid by well known methods, and a Lewis acid catalyst such as tin tetrachloride. In general, the appropriate organic carboxylic acids needed for this reaction are known, commercially available, or readily prepared by those of ordinary skill in the art.

In the processes described herein for the preparation of compounds of the subject invention, requirements for protective groups on reactive moieties are well recognized by one skilled in the art of organic chemistry; accordingly, the use of appropriate protecting groups is included in the processes disclosed herein, even if not expressly depicted in all schemes and examples. Introduction and removal of such suitable protecting groups, e.g., for N, S and O, are disclosed, for example, in the following references: McOmie, J. F. W., "Protective Groups in Organic Chemistry", *Advances in Organic Chemistry*, Vol. 3 (1963), pp. 159–190; and Greene, T. W., P. G. M. Wuts, *Protecting Groups in Organic Synthesis*, Wiley (New York), 1991.

The following non-limiting examples provide further information regarding synthesis of the subject compounds.

EXAMPLE 1

1-(7-tert-Butyl-3,3-dimethyl-2,3-dihydrobenzo[b]furan-5-yl)-4-cyclopropylbutan-1-one

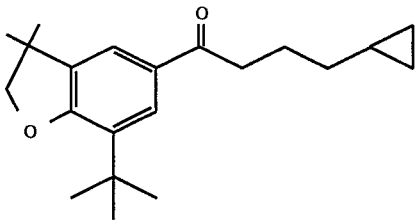

2,4-dibromo-6-tert-butylphenol. In a 2 L 3-neck flask, equipped with Ar inlet, reflux condenser, addition funnel, and efficient magnetic stir bar, is placed 2-tert-butylphenol (150.2 g, 1.00 mol) and MeOH (300 mL). The stirred solution is cooled in an ice bath as neat $Br_2$ (321.6 g, 2.01 mol, 2.01 eq) is added dropwise over 0.5 h (Caution: this reaction is exothermic. Control with rate of addition.) The reaction is monitored by TLC (2% EtOAc/hexane), and is complete after 2 hrs. The reaction mixture is transfered to a 1 L beaker, along with a 20-mL rinse of the reaction flask. The red solution solidifies rapidly to a bright orange crystalline mass. The crystalline mass is redissolved by heating over a steam bath, and then a solution of $Na_2S_2O_5$ (1.45 g, 5.4 mmol) in 40 mL $H_2O$ is added, followed immediately by fresh MeOH (60 mL). The resulting suspension is reheated on the steam bath for 10 min (the mixture does not redissolve), and then is vigorously stirred while allowing to cool to room temperature. After 0.5 h, practically all yellow color has vanished, and faint orange-white crystals are deposited. These are filtered and air dried to yield 2,4-dibromo-6-tert-butylphenol as faint orange-white platelets.

2,4-dibromo-6-tert-butylphenyl isobutenyl ether. In a 3000 mL 3-neck flask, equipped with Ar inlet and magnetic stirrer, is placed 2,4-dibromo-6-tert-butylphenol (70.0 g, 226 mmol), $K_2CO_3$ (37.6 g, 276 mmol, 1.2 eq), NaI (3.38 g, 22.6 mmol, 0.1 eq), p-methallyl chloride (33.9 mL, 339 mmol, 1.5 eq), and acetone (1500 mL). The reaction mixture is vigorously stirred at 23° C. for 56 hrs, and monitored by TLC analysis (pet. ether). The solids are removed by filtration, washed with acetone, and the filtrates rotoevaporated (bath temperature kept below 35° C.) to give an oil. The oil is dissolved in hexane (100 mL), and stirred with silica gel (80 g). The slurry is filtered through a pad of Celite, and eluted with additional hexane (6×100 mL). The filtrate is evaporated to give 2,4-dibromo-6-tert-butylphenyl isobutenyl ether as a yellow oil. The material is stored in the freezer and is used as soon as possible.

7-tert-butyl-3,3-dimethyl-2,3-dihydrobenzo[b]furan. Anhydrous hypophosphorus acid (275 g, 4.16 mol) is prepared by azeotropically removing water from commercial 50% aqueous solution (550 g) using toluene (5×500 mL). Caution: perform behind a shatter-proof shield, since a sudden pressure increase occasionally occurs. In a 5000 mL 3-neck flask, equipped with Ar bubbler and submersed Ar inlet, reflux condenser, addition funnel, and magnetic stirrer is placed dioxane (3000 mL), 2,4-dibromo-6-tert-butylphenyl isobutenyl ether (50.3 g, 0.14 mol), the anhydrous hypophosphorus acid (275 g, 4.16 mol) prepared above, and triethylamine (585 mL, 4.16 mol). An exotherm to 50° C. is apparent. The mixture is degassed by bubbling with Ar for 30 min, and then is maintained under an atmosphere of Ar. A solution of azo-bis-isobutyrylnitrile (AIBN) (20 mL of a 0.7M solution in de-gassed dioxane) is added via the addition funnel. The stirred solution is brought to reflux. Every 0.5 h, an additional 20 mL of the AIBN solution is added. The reaction is monitored by TLC for disappearance of starting material. After 3 h, further addition of AIBN is discontinued, the reaction is allowed to reflux an additional 14 h, and then is allowed to cool to 24° C. The reaction is twice extracted with a mixture of brine (250 mL) and 1N HCl (100 mL). The organic layer is dried over $MgSO_4$, filtered, and evaporated to give a yellow oil admixed with a white solid. This is triturated with hexane (300 mL), and the insolubles are filtered off, rinsed with fresh hexane (50 mL), and discarded. The hexanes are evaporated to give a clear yellow oil. Distillation, followed by hydrogenation using 20% by weight of 10% Pd/C and 50 psi $H_2$ atmosphere in EtOH solution (0.6 g/mL) for 14 h results in complete dehalogenation to yield 7-tert-butyl-3,3-dimethyl-2,3-dihydrobenzo[b]furan.

4-cyclopropanebutan-1-ol. In a 500 mL 3-neck flask, equipped with Ar inlet, magnetic stirrer, reflux condensor, and septum, is placed 5-hexen-1-ol (25 g, 0.25 mol), diiodomethane, (25.2 mL, 83.8 g, 0.31 mol, 1.25 eq), and $CH_2Cl_2$ (150 mL). The solution is cooled in an ice bath, and neat $AlMe_3$ (Caution: extremely pyrophoric) (52 mL, 39.6 g, 0.55 mol, 2.2 eq) is added (Caution: strong exotherm and gas evolution) via canula over 20 min. After 1 h at 0° C., the reaction mixture is warmed at 35° C. for 14 h. The solution is cooled in an ice bath, and 1.5N NaOH (1000 mL) is added gradually (Caution: violent exotherm), followed by $H_2O$ (1000 mL). The mixture is extracted with $CH_2Cl_2$ (3×250 mL). The organic layers are dried ($MgSO_4$), filtered, and evaporated to a yellow oil. This 4-cyclopropanebutan-1-ol is used in the next reaction without further purification.

4-cyclopropylbutanoic acid. Jones reagent is prepared by carefully adding $H_2SO_4$ (321 mL) to a cold solution of $CrO_3$ (366 g) in $H_2O$ (600 mL) over a period of 0.5 h. In a 5-L 3-neck flask, equipped with mechanical stirrer, internal thermometer, and 1-L addition funnel is placed a solution of 4-cyclopropylbutan-1-ol (127.0 g) in acetone (300 mL). Stirring is commenced, and the solution is cooled below –10° C. with an ice/MeOH bath. The Jones reagent is added at a rate such that the temperature of the reaction mixture never exceeds +10° C. The reaction mixture becomes dark green and heterogenous. 300 mL of Jones reagent is added over 3.5 h and the reaction appears to be complete by TLC (hexane:EtOAc:HOAc, 3:1:0.05). An additional 50 mL Jones reagent is added, and the red color of the reagent persists. The reaction is quenched by the addition of isopropanol (80 mL), and the mixture is allowed to warm to 23° C. A small amount of green precipitate is filtered off, rinsed with acetone (3×200 mL), and discarded. The filtrate is evaporated to a biphasic mixture, poured onto 1.8 kg ice/water, and made alkaline to indicator paper with 50 wt % NaOH (133 g) added in portions. The resulting green solution is filtered to remove a small amount of solids which are discarded. The filtrate is extracted with Et20 (2×40 mL), and the Et20 layers are dried and evaporated to yield 4-cyclopropylbutyl 4-cyclopropylbutanoate. The aqueous layer is cooled in ice while it is acidified with 12N HCl (139 g). The resulting solution is extracted with EtOAc (3×1 L). The aqueous layer is discarded. The organic phases are combined, dried over $MgSO_4$, filtered through paper and evaporated to yield 4-cyclopropylbutanoic acid as a faint green oil. This can be further purified by filtration through Celite and distillation at reduced pressure (0.2–0.4 mbar, 60°–90° C.).

1-(7-tert-butyl-3,3-dimethyl-2,3-dihydrobenzo[b]furan-5-yl)-4-cyclopropylbutan-1-one. In a 50 mL 3-neck flask equipped with magnetic stir bar, Ar inlet, and septum inlet, is placed 3,3-dimethyl-2,3-dihydrobenzo[b]furan (5.39 g, 26.4 mmol), 4-cyclopropylbutanoic acid (3.33 g, 26.4 mmol), and $CH_2Cl_2$ (10 mL). The solution is cooled to –20° C., and then trifluoroacetic anhydride (4.10 mL, 29.0 mmol) (freshly distilled) is added. After 7 h at this temperature, the reaction is allowed to warm to 25° C. and quenched with $H_2O$ (20 mL). The aqueous layer is extracted with fresh $CH_2Cl_2$ (3×20 mL) and discarded. The combined organic layers are dried ($MgSO_4$), filtered, and evaporated to a dark oil (9.05 g) which is purified by column chromatography over $SiO_2$ (200 g) using hexane and then 2% EtOAc in hexane as eluent, to provide 1-(7-tert-butyl-3,3-dimethyl-2,3-dihydrobenzo[b]furan-5-yl)-4-cyclopropylbutan-1-one as a faint yellow oil.

Utilizing substantially the method of Example 1 (and making suitable substitutions for the appropriate carboxylic acid) the following subject compounds of Examples 2–12 are obtained.

EXAMPLE 2

1-(7-tert-Butyl-3,3-dimethyl-2,3-dihydrobenzo[b]furan-5-yl)-ethan-1-one

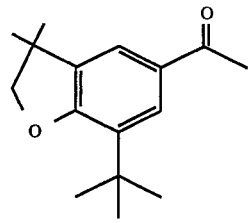

EXAMPLE 3

1-(7-tert-Butyl-3,3-dimethyl-2,3-dihydrobenzo[b]furan-5-yl)-cyclopropylmethanone

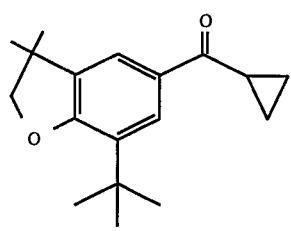

EXAMPLE 4

1-(7-tert-Butyl-3,3-dimethyl-2,3-dihydrobenzo[b]furan-5-yl)-2-methylpropan-1-one

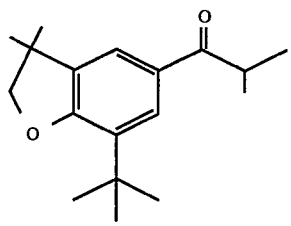

EXAMPLE 5

1-(7-tert-Butyl-3,3-dimethyl-2,3-dihydrobenzo[b]furan-5-yl)-propan-1-one

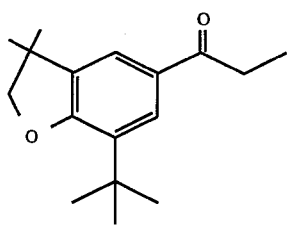

EXAMPLE 6

1-(7-tert-Butyl-3,3-dimethyl-2,3-dihydrobenzo[b]furan-5-yl)-butan-1-one

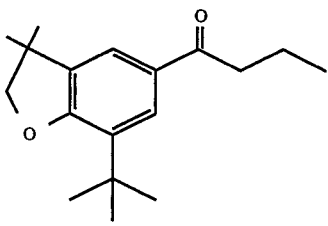

EXAMPLE 7

1-(7-tert-Butyl-3,3-dimethyl-2,3-dihydrobenzo[b]furan-5-yl)-pentan-1-one

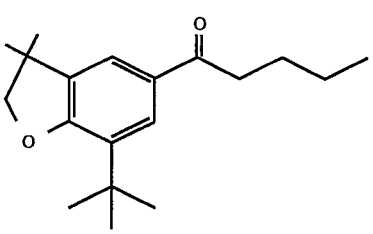

EXAMPLE 8

1-(7-tert-Butyl-3,3-dimethyl-2,3-dihydrobenzo[b]furan-5-yl)-hexan-1-one

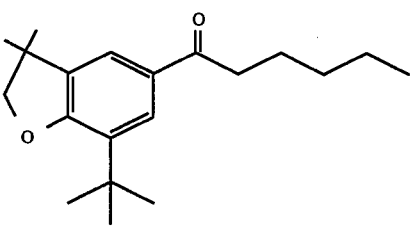

EXAMPLE 9

1-(7-tert-Butyl-3,3-dimethyl-2,3-dihydrobenzo[b]furan-5-yl)-cyclohexylmethanone

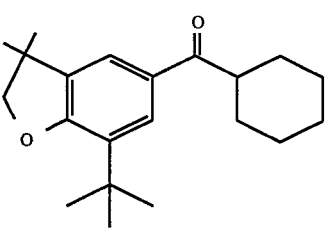

EXAMPLE 10

1-(7-tert-Butyl-3,3-dimethyl-2,3-dihydrobenzo[b]furan-5-yl)-cyclopentylmethanone

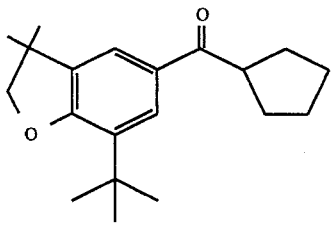

EXAMPLE 11

1-(7-tert-Butyl-3,3-dimethyl-2,3-dihydrobenzo[b]furan-5-yl)-2-methylcyclopropylmethanone

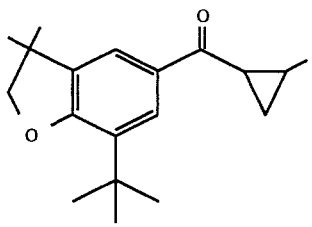

EXAMPLE 12

1-(7-tert-Butyl-3,3-dimethyl-2,3-dihydrobenzo[b]furan-5-yl)-3-methyl-2-buten-1-one

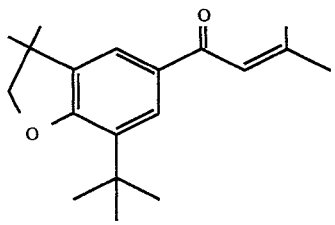

EXAMPLE 13

1-(7-tert-Butyl-3,3-dimethyl-2,3-dihydrobenzo[b]furan-5-yl)-3-chloro-3-methyl-butan-1-one

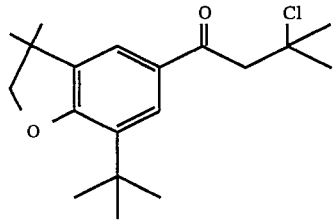

A solution of 1-(7-tert-butyl-3,3-dimethyl-2,3-dihydrobenzo[b]furan-5-yl)-3-methyl-2-buten-1-one (Example 12) (2.0 g, 6.2 mmol) in HCl-saturated Et$_2$O (30 mL) is stirred at 25° C. overnight. The solution is treated with H$_2$O (20 mL), and partitioned against CH$_2$Cl$_2$ (3×20 mL). The combined organic layers are dried (MgSO$_4$), filtered, and evaporated to a cream-colored solid which is crystallized from hexane to give 1-(7-tert-butyl-3,3-dimethyl-2,3-dihydrobenzo[b]furan-5-yl)-3-chloro-3-methylbutan-1-one.

EXAMPLE 14

1-(7-tert-Butyl-3,3-dimethyl-2,3-dihydrobenzo[b]furan-5-yl)-3-hydroxy-3-methylbutan-1-one

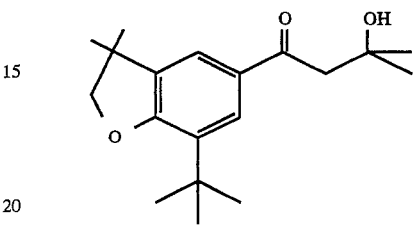

A solution of 1-(7-tert-butyl-3,3-dimethyl-2,3-dihydrobenzo[b]furan-5-yl)-ethan-1-one (Example 2) (1.07 g, 4.3 mmol) in CH$_2$Cl$_2$ (65 mL) is cooled to −78° C., and diisopropylethylamine (0.97 mL, 5.6 mmol) and trimethylsilyltriflate (1.08 mL, 5.6 mmol) are added sequentially via syringe. The reaction is stirred at −78° C. for 10 min and then is allowed to warm to 24° C. and is stirred at that temperature for 45 min. The solution is once again cooled to −78° C., and acetone (0.54 mL, 4.3 mmol) is added, followed by TiCl$_4$ (1M solution in CH$_2$Cl$_2$, 4.3 mL, 4.3 mmol). After 1 h at −78° C., the reaction mixture is allowed to warm to 24° C. and evaporated. The residue is partioned between MeOH/1N HCl and CH$_2$Cl$_2$. The CH$_2$Cl$_2$ layer is dried (MgSO$_4$), filtered, evaporated, and chromatographed over SiO$_2$ using EtOAc/hexane (1:6), to yield 1-(7-tert-butyl-3,3-dimethyl-2,3-dihydrobenzo[b]furan-5-yl)-3-hydroxy-3-methylbutan-1-one.

Utilizing substantially the method of Example 14 (and making suitable substitution for the appropriate ketone) the subject compound of Example 15 is obtained.

EXAMPLE 15

1-(7-tert-Butyl-3,3-dimethyl-2,3-dihydrobenzo[b]furan-5-yl)-2-(1-hydroxycyclopentyl)-ethan-1-one

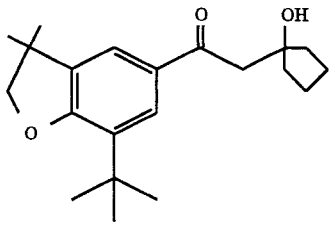

EXAMPLE 16

1-(7-tert-Butyl-3,3-dimethyl-2,3-dihydrobenzo[b]furan-5-yl)-3-(N,N-dimethylamino)propen-1-one

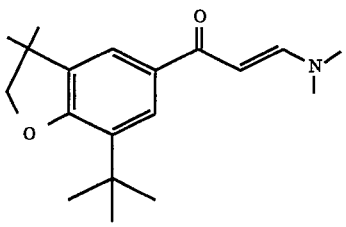

A solution of 1-(7-tert-butyl-3,3-dimethyl-2,3-dihydrobenzo[b]furan-5-yl)-ethan-1-one (Example 2) (1.54 g, 6.25 mmol) in dimethylformamide dimethylacetal (15 mL) is heated at reflux for 17 h. The reaction mixture is evaporated, and the yellow residue is crystallized from hexanes to give 1-(7-tert-butyl-3,3-dimethyl-2,3-dihydrobenzo[b]furan-5-yl)-3-(N,N-dimethylamino)propen-1-one.

EXAMPLE 17

1-(7-tert-Butyl-3,3-dimethyl-2,3-dihydrobenzo[b]furan-5-yl)-3-mercapto-3-methylbutan-1-one

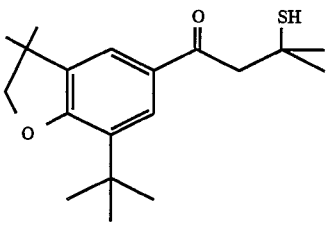

1-(7-tert-butyl-3,3-dimethyl-2,3-dihydrobenzo[b]furan-5-yl)-3-(thiomethyl(4'-methoxyphenyl))-3-methylbutan-1-one. To a solution of 1-(7-tert-butyl-3,3-dimethyl-2,3-dihydrobenzo[b]furan-5-yl)-3-methyl-2-buten-1-one (Example 12) (2.19 g, 7.6 mmol) in benzene (70 mL) is added piperidine (0.08 mL, 0.76 mmol), and 4-methoxybenzylthiol. The resulting yellow solution is allowed to stir for 56 hours, and then additional piperidine (0.08 mL, 0.76 mmol) is added; and stirring is continued an additional 17 h. The solvent is evaporated, and the resulting oil is chromatographed over SiO₂ using hexane to yield 1-(7-tert-butyl-3,3-dimethyl-2,3-dihydrobenzo[b]furan-5-yl)-3-(thiomethyl-(4'-methoxyphenyl))-3-methylbutan-1-one as a white solid.

1-(7-tert-butyl-3,3-dimethyl-2,3-dihydrobenzo[b]furan-5-yl)-3-mercapto-3-methylbutan-1-one. In a Teflon hydrogen fluoride handling apparatus, equipped with stir bar and external cold bath, a solution of 1-(7-tert-butyl-3,3-dimethyl-2,3-dihydrobenzo[b]furan-5-yl)-3-(thiomethyl(4'-methoxyphenyl))-3-methylbutan-1-one (1.12 g, 2.5 mmol) in para-cresol (2.5 mL) and para-thiocresol (2.5 mL) is cooled to 0° C., and treated with neat hydrogen fluoride (approximately 50 mL) for 1 hour. The hydrogen fluoride is removed under vacuum. The resulting dark oil is applied to a column of SiO₂ and eluted with hexane to remove dark-colored impurities. The resulting oil (972 mg) is chromatographed repeatedly on neutral alumina, and finally crystallized from EtOH to provide 1-(7-tert-butyl-3,3-dimethyl-2,3-dihydrobenzo[b]furan-5-yl)-3-mercapto-3-methylbutan-1-one as a white solid.

EXAMPLE 18

1-(7-Cyclopentyl-3,3-dimethyl-2,3-dihydrobenzo[b]furan-5-yl)-4-cyclopropyl butan-1-one

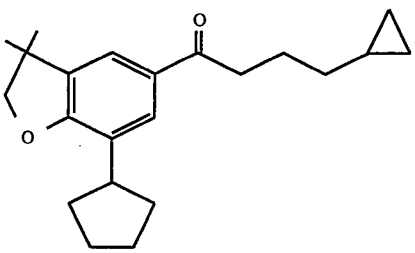

2,4-dibromo-6-cyclopentylphenol. A solution of 2-cyclopentyl phenol (24 g, 149 mmol) in MeOH (50 mL) is cooled to 0° C., and Br₂ (22.9 mL, 446 mmol) is added dropwise over 1 h. The reaction is allowed to warm to 24° C. and stir for 72 h. Then H₂O (50 mL) is added, and the MeOH is rotovaped off. The resulting mixture is extracted with CH₂Cl₂ (3×50 mL). The organic layers are combined, dried (MgSO₄), and evaporated to yield dark red oil, which is mixed with SiO₂ (5 g) and hexane (30 mL), filtered, and once again evaporated to provide 2,4-dibromo-6-cyclopentylphenol suitably pure for the next step.

2,4-dibromo-6-cyclopentyl isobutenyl ether. Substantially the method described in Example 1 is employed for the reaction between 2,4-dibromo-6-cyclopentylphenol and 3-chloro-2-methylpropene, to provide 2,4-dibromo-6-cyclopentyl isobutenyl ether as a colorless oil.

7-cyclopentyl-3,3-dimethyl-2,3-dihydrobenzo[b]furan. To a solution of 2,4-dibromo-6-cyclopentyl isobutenyl ether (37.9 g, 102 mmol) in dimethylformamide (1200 mL) is added palladium acetate (1.14 g, 5.1 mmol), and triphenylphosphine (1.34 g, 5.1 mmol) The mixture is deoxygenated by bubbling with N₂ for 15 minutes, and is heated to 70° C. A deoxygenated solution of piperidine (0.34M) and formic acid (0.26M) in dimethylformamide is injected via syringe pump at a rate of 0.9 mL/min. After 250 mL had been injected, the reaction is complete by GC analysis. The reaction is allowed to stir under N₂ at 70° C. for 14 h. After cooling to 24° C., the reaction is poured onto H₂O (1500 mL) and extracted extensively with hexane (6×2000 mL). The aqueous dimethylformamide layer is discarded, and the hexanes are concentrated and partitioned against 1N NaOH (3×150 mL). The hexane layer is washed with H₂O (150 mL), dried (MgSO₄), filtered and evaporated to yield 7-cyclopentyl-3,3-dimethyl-2,3-dihydrobenzo[b]furan as an oil.

1-(7-cyclopentyl-3,3-dimethyl-2,3-dihydrobenzo[b]furan-5-yl)-4-cyclopropylbutan-1-one. Substantially the method described in Example 1 is employed for the reaction between 7-cyclopentyl-3,3-dimethyl-2,3-dihydrobenzo[b]furan and 4-cyclopropylbutanoic acid to provide 7-cyclopentyl-3,3-dimethyl-2,3-dihydrobenzo[b]furan as a colorless oil.

EXAMPLE 19

1-(7-tert-Butyl-2,3-dihydrobenzo[b]furan-5-yl)-pentan-1-one

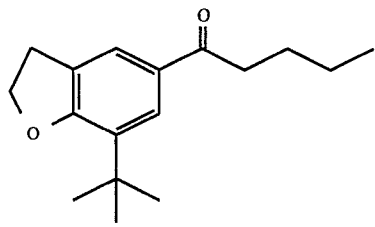

1,5-dibromo-(2-bromoethoxy)-3-tert-butylbenzene. To a solution of 2,4-dibromo-6-tert-butylphenol (5.00 g, 16.2 mmol) in acetone (70 mL) is added 1,2-dibromoethane (2.80 mL, 32.5 mmol) and $K_2CO_3$ (6.70 g, 48.7 mmol). The mixture is heated at reflux for 14 h, and then is filtered and evaporated. The residue is purified by chromatography over $SiO_2$ eluting with hexanes. The resulting oil is distilled to give 1,5-dibromo-(2-bromoethoxy)-3-tert-butylbenzene as a pale yellow oil.

7-tert-butyl-2,3-dihydrobenzor[b]furan. A cold solution of 1,5-dibromo-2-(2-bromoethoxy)-3-tert-butylbenzene (5.00 g, 12.05 mmol) in tetrahydrofuran/hexane (100 mL/20 mL) is cooled to −95° C. (MeOH/$Et_2O$, liquid $N_2$). A solution of n-butyl lithium in hexane (12 mL, 30.1 mmol) is added dropwise, and the reaction is allowed to stir for 0.5 h between −95° C. and −80° C. After 4 h, the reaction is poured onto saturated $NH_4Cl$, and extracted with ethylacetate. The organic layer is washed twice with $H_2O$ and once with brine. The combined organic layers are dried ($MgSO_4$), filtered, and evaporated. The resulting oil is purified by chromatography over $SiO_2$ using hexanes. The resulting oil is distilled at reduced pressure to give 7-tert-butyl-2,3-dihydrobenzo[b]furan as a low melting white solid.

1-(7-tert-butyl-2,3-dihydrobenzo[b]furan-5-yl)-butan-1-one. Substantially the method described in Example 1 is employed for the reaction between 7-tert-butyl-2,3-dihydrobenzo[b]furan and pentanoic acid, to provide 1-(7-tert-butyl-2,3-dihydrobenzo[b]furan-5-yl)-butan-1-one as a colorless oil.

Using substantially the method of Example 19, the compounds of Examples 20 through 23 are prepared by reaction of 7-tert-butyl-2,3-dihydrobenzo[b]furan and the appropriate carboxylic acid.

EXAMPLE 20

1-(7-tert-Butyl-2,3-dihydrobenzo[b]furan-5-yl)-3-methyl-2-buten-1-one

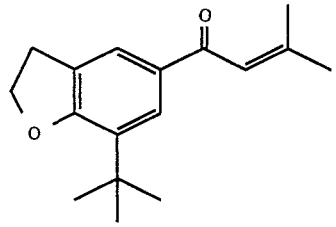

EXAMPLE 21

1-(7-tert-Butyl-2,3-dihydrobenzo[b]furan-5-yl)-4-cyclopropylbutan-1-one

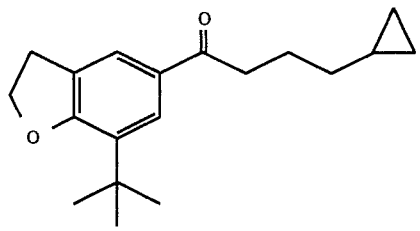

EXAMPLE 22

1-(7-tert-Butyl-2,3-dihydrobenzo[b]furan-5-yl)-2-methylpropan-1-one

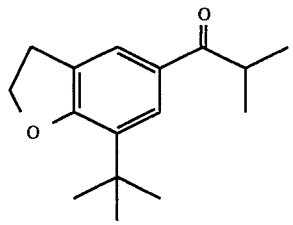

EXAMPLE 23

1-(7-tert-Butyl-2,3-dihydrobenzo[b]furan-5-yl)-propan-1-one

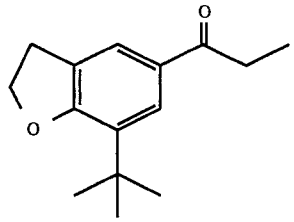

EXAMPLE 24

1-(7-tert-Butyl-3,3-dimethyl-2,3-dihydrobenzo[b]thiophen-5-yl)-butan-1-one

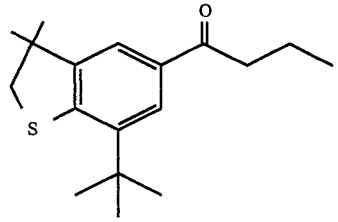

2-bromo-6-tert-butylthiophenol. To a solution of freshly distilled tetramethylethylenediamine (7.5 mL, 50 mmol) in dry cyclohexane (35 mL) is added dropwise at 24° C. a solution of n-butyl lithium in hexanes (31 mL, 50 mmol). After addition is complete, the reaction mixture is cooled to 0° C. A solution of 2-tert-butylthiophenol (3.77 g, 22.7 mmol) in dry cyclohexane (10 mL) is added at a rate such that the reaction temperature stays below 10° C. The reaction is allowed to stir at 24° C. for 14 h. A solution of sec-butyl lithium in hexanes (17.5 mL, 22.7 mmol) is added at this temperature, and the color of the reaction changes from yellow to orange. After 1 h, the reaction mixture is added at −78° C. to a solution of 1,2-dibromotetrafluoroethane (5.4 mL, 45.4 mmol) in dry tetrahydrofuran (100 mL). The mixture is allowed to warm to 24° C., and is partitioned against 0.1N HCl (100 mL). The organic phase is dried (MgSO₄), filtered and evaporated to give 2-bromo-6-tert-butylthiophenol as a yellow oil.

2-bromo-6-tert-butylphenyl isobutenyl thioether. A mixture of 2-bromo-6-tert-butylthiophenol (6.04 g, 22.7 mmol), K₂CO₃ (3.76 g, 27.2 mmol), NaI (0.34 g, 2.27 mmol), and 3-chloro-2-methylpropene (2.3 mL, 22.7 mmol) in acetone (125 mL) is heated at reflux for 3 h. The reaction is allowed to cool to 24° C. The solids are filtered and discarded, and the filtrate is evaporated to a biphasic oil. The upper light colored layer is separated, taken up in hexane (50 mL), and treated with SiO₂ (5 g). Filtration and evaporation provides 2-bromo-6-tert-butylphenyl isobutenyl thioether as a yellow oil.

3,3-dimethyl-7-tert-butyl-2,3-dihydrobenzo[b]thiophene. A solution of 2-bromo-6-tert-butylphenyl isobutenyl thioether (600 mg, 2.07 mmol), 90% hypophosphorous acid (4.4 g, 60 mmol), and triethylamine (8.4 mL, 60 mmol) in dioxane (30 mL) is deoxygenated by bubbling with N₂ for 20 min. The solution is then heated under N₂ to reflux, and a solution of azo-bis-isobutyrylnitrile (205 mg, 1.04 mmol) in deoxygenated dioxane (2 mL) is added in 0.2-mL portions over 3 h. The reaction is allowed to cool to 24° C., and 1N HCl (40 mL) and brine (30 mL) are added. The mixture is extracted with Et₂O (3×50 mL), and the ethereal layers are back extracted with 1N NaOH (40 mL). The organic phase is dried (MgSO₄), filtered and evaporated to a yellow oil. Kugelrohr distillation provides 3,3-dimethyl-7-tert-butyl-2,3-dihydrobenzo[b]thiophene as a colorless oil.

1-(7-tert-butyl-3,3-dimethyl-2,3-dihydrobenzo[b]thiophen-5-yl)-butan-1-one. Substantially the method described in Example 1 is employed for the reaction between 7-tert-butyl-3,3-dimethyl-2,3-dihydrobenzo[b]thiophene and butanoic acid, to provide 1-(7-tert-butyl-3,3-dimethyl-2,3-dihydrobenzo[b]thiophen-5-yl)-butan-1-one as a colorless oil.

Using substantially the method of Example 24, the compounds of Examples 25 and 26 are prepared by reaction of 7-tert-butyl-3,3-dimethyl-2,3-dihydrobenzo[b]thiophene and the appropriate carboxylic acid.

EXAMPLE 25

1-(7-tert-Butyl-3,3-dimethyl-2,3-dihydrobenzo[b]thiophen-5-yl)-pentan-1-one

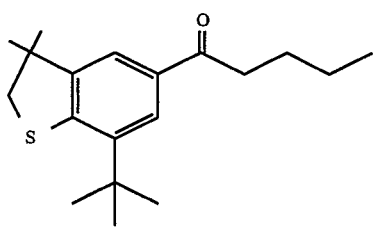

EXAMPLE 26

1-(7-tert-Butyl-3,3-dimethyl-2,3-dihydrobenzo[b]thiophen-5-yl)-4-cyclopropylbutan-1-one

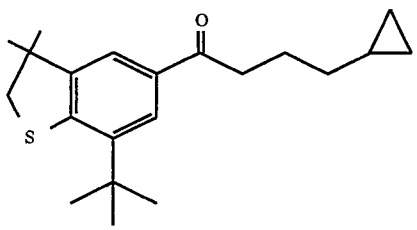

EXAMPLE 27

1-(7-tert-Butyl-3,3-dimethyl-2,3-dihydrobenzo[b]furan-5-yl)-phenylmethanone

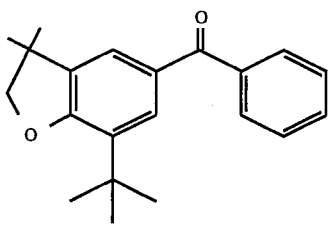

Utilizing substantially the method of Example 1.

EXAMPLE 28

1-(3,3-Dimethyl-2,3-dihydrobenzo[b]furan-5-yl)-4-cyclopropylbutan-1-one

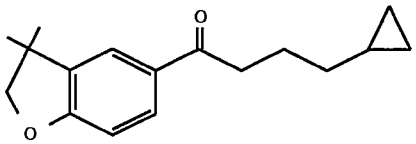

Utilizing substantially the method of Example 1.

EXAMPLE 29

1-(3,3-Dimethyl-2,3-dihydrobenzo[b]furan-5-yl)-3-hydroxy-3-methylbutan-1-one

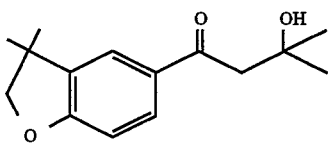

Utilizing substantially the method of Example 14.

EXAMPLE 30

1-(7-tert-Butyl-3,3-dimethyl-2,3-dihydrobenzo[b]furan-5yl)-2-acetylthioethan-1-one

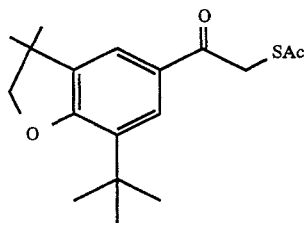

A mixture of 1-(7-tert-butyl-3,3-dimethyl-2,3-dihydrobenzo[b]furan-5yl)-2-bromoethan-1-one (0.63 g, 1.9 mmol) and potassium thioacetate (0.22 g, 1.9 mmol) in 10 mL of anhydrous acetone is heated at reflux for 2 h. Acetone is removed under reduced pressure and the residue is partitioned between ether and water; the ethereal layer is dried over anhydrous magnesium sulfate and concentrated in vacuo. Purification by flash column chromatography on silica gel (10% ethyl acetate-hexane) gives 0.31 g of the title compound initially as a yellowish oil which upon storage in refrigerator became a light yellow solid (mp 61°–63° C.).

EXAMPLE 31

1-(7-tert-Butyl-3,3-dimethyl-2,3-dihydrobenzo[b]furan-5-yl)-2-ethylthioethan-1-one

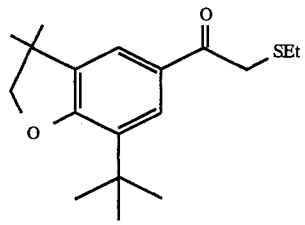

1-(7-tert-Butyl-3,3-dimethyl-2,3-dihydrobenzo[b]furan-5-yl)-2-chloroethan-1-one. A mixture of benzyltrimethylammonium dichloroiodate (18.18 g, 52.2 mmol), 1-(7-tert-butyl-3,3-dimethyl-2,3-dihydrobenzo[b]furan-5-yl)-ethan-1-one (6.65 g, 27.0 mmol), 325 mL of 1,2-dichloroethane, and 130 mL of methanol is heated at reflux for 1.5 h. The reaction mixture is cooled to room temperature and concentrated in vacuo; 5% aqueous sodium bisulfite solution (126 mL) is added to the residue obtained. This mixture is extracted with ether and the extract is dried over anhydrous magnesium sulfate and concentrated to afford 8.38 g of the title compound as a reddish solid.

1-(7-tert-Butyl-3,3-dimethyl-2,3-dihydrobenzo[b]furan-5-yl)-2-ethylthioethan-1-one. Sodium thioethoxide (0.54 g, 6.4 mmol) is added in portions to a solution of 1-(7-tert-butyl-3,3-dimethyl-2,3-dihydrobenzo[b]furan-5-yl)-2-chloroethan-1-one (1.12 g, 4.0 mmol) in 30 mL of methanol at room temperature. The reaction is stirred for 2.5 h, and concentrated in vacuo. The residue is dissolved in ether, washed with water and with brine, dried over anhydrous magnesium sulfate, and concentrated to give 1.12 g of the crude product. Purification by flash column chromatography on silica gel (5% ethyl acetate-hexane) afforded 0.72 g of the title compound as a light yellow oil.

EXAMPLE 32

1-(7-tert-Butyl-3,3-dimethyl-2,3-dihydrobenzo[b]furan-5-yl)-3-thia-butan-1-one

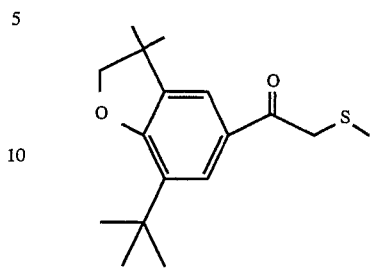

Utilizing substantially the method of Example 1.

EXAMPLE 33

1-(7-tert-Butyl-3,3-dimethyl-2,3-dimethyl-23-dihydrobenzo[b]furan-5-yl)-3-sulfinylbutan-1-one

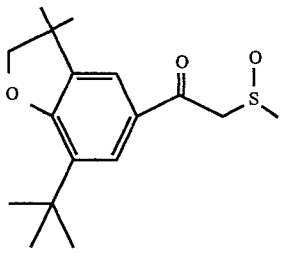

1-(7-tert-Butyl-3,3-dimethyl-2,3-dihydrobenzo[b]furan-5-yl)-3-thiabutan-1-one (Example 32, 1.08g, 3.70 mmol) in 7.5 mL of $CH_2Cl_2$ is cooled to 0° C. and m-chloroperbenzoic acid (826 mg, 4.07 mmol) is added. After stirring for 45 min, the reaction is poured into 15 mL of saturated bicarbonate diluted with 15 mL of water and was extracted with $CH_2Cl_2$. The combined extracts are dried with molecular sieves and evaporated. The crude product is purified by column chromatography on silica with 10->50% EtOAc in hexane followed by 100% acetone. The resulting white solid was recrystallized from EtOAc/hexanes to provide 1-(7-tert-butyl-3,3-dimethyl-2,3-dihydrobenzo[b]furan-5-yl)-3-sulfinylbutan-1-one Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.1% to about 99.9% by weight of a compound, more preferably from about 20% to about 80%, and most preferably from about 40% to about 70%.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a subject compound is basically determined by the way the compound is to be administered.

If the subject compound is to be injected, it is preferably injected non-intravenously; the preferred pharmaceutically-acceptable carrier is sterile, physiological saline, with blood compatible suspending agent, the pH of which has been adjusted to about 7.4. Such injectable compositions preferably comprise from about 1% to about 50% of the subject compound, more preferably from about 5% to about 25%, also preferably from about 10 mg to about 600 mg of the subject compound per dose.

Suitable pharmaceutically-acceptable carriers for topical application include those suited for use in lotions, creams, gels and the like. Topical compositions preferably contain from about 1% to about 50% of an emollient, more preferably from about 5% to about 25% of an emollient. Such topical compositions preferably comprise from about 0.1% to about 50%, of the subject compound, more preferably from about 0.5% to about 10%, also preferably from about 5 mg to about 1000 mg per dose.

The preferred mode of administering the subject compound is perorally. The preferred unit dosage form is therefore tablets, capsules and the like, comprising a safe and effective amount of the compound, which is preferably from about 5 mg to about 3500 mg, more preferably from about 10 mg to about 1000 mg, and most preferably from about 25 mg to about 600 mg.

Many of the subject compounds are hydrophobic. If it is desired to provide an aqueous-based composition or a composition soluble in or miscible with aqueous media, a solubilizing agent may be included in the composition. Non-limiting examples of such solubilizing agents include polyethylene glycol, propylene glycol, ethanol, and polyoxyethylene (35) castor oil.

Particularly preferred oral composition carriers suitable for compositions of the subject invention are disclosed in Kelm & Bruns U.S. Pat. No. 5,189,066, issued Feb. 23, 1993, entitled "Pharmaceutical Compositions of Tebufelone", and Kelm & Debrozsi U.S. Pat. No. 5,281,420, issued Jan. 25, 1994, entitled "Solid Dispersion Compositions of Tebufelone", hereby incorporated herein by reference.

Another aspect of the subject invention is methods for treating or preventing diseases characterized by inflammation by administering a safe and effective amount of a subject compound to a human or lower animal in need of such treatment. The term "diseases characterized by inflammation", as used herein, means conditions which are known to involve inflammation, and may include conditions such as arthritis (e.g., rheumatoid arthritis, osteoarthritis, psoriatic arthritis, juvenile arthritis, Reiter's syndrome, infectious arthritis, and ankylosing spondylitis, systemic lupus, erythematosus and gout), as well as the presence of inflammation whether or not it is associated with an identifiable disease. Diseases characterized by inflammation further may include inflammation in the oral cavity (e.g., inflammation associated with gingivitis or periodontal disease); inflammation in the gastrointestinal tract, (e.g., inflammation associated with ulcers and irritable bowel disease); inflammation associated with dermatological diseases (e.g., psoriasis, acne, and other skin inflammation); inflammation associated with the respiratory tract (e.g., asthma, bronchitis, and allergies); and inflammation in the central nervous system (e.g., Alzheimer's disease).

Another aspect of the subject invention is methods for treating or preventing pain by administering a safe and effective amount of a subject compound to a human or lower animal in need of such treatment. Pain which can be treated or prevented by administering the subject compounds may include peripheral pain, menstrual pain, dental pain, and lower back pain.

Another aspect of the subject invention is methods for preventing oxidative damage at inflammatory sites by administering a safe and effective amount of a subject compound to a human or lower animal in need of such treatment. While not limited to a particular mechanism, it is believed that the subject compounds inhibit leukotriene synthesis, thereby decreasing neutrophil accumulation at an inflammatory site.

Another aspect of the subject invention is methods for treating or preventing gastric or duodenal ulcers or erosions by administering a safe and effective amount of a subject compound to a human or lower animal in need of such treatment. In particular, such ulcers or erosions caused by ethanol or non-steroidal antiinflammatory drugs (NSAIDs) can be treated and/or prevented by administration of preferred subject compounds.

Appropriate tests for determining the gastrointestinal safety or gastroprotective properties of the subject compounds are known.

Methods for determining acute gastrointestinal safety are disclosed and/or referred to in the following references: Unangst, P. C., G. P. Shrum, D. T. Connor, R. D. Dyer, and D. J. Schrier, "Novel 1,2,4-Oxadiazoles and 1,2,4-Thiadiazoles as Dual 5-Lipoxygenase and Cyclooxygenase Inhibitors", *J. Med. Chem.*, Vol. 35 (1992), pp. 3691–3698; and Segawa, Y. O. Ohya, T. Abe, T. Omata, et al., "Anti-inflammatory, Analgesic, and Antipyretic Effects and Gastrointestinal Toxicity of the New Anti-inflammatory Drug N-{3-[3-(piperidinylmethyl)phenoxy]propyl}-carbamoylmethylthio]ethyl 1-(p-chlorobenzoyl) 5-Methoxy-2methyl-3-indolylacetate", *Arzneim.-Forsch./*

*Drug Res.*, Vol. 42 (1992), pp. 954–992. In the methods disclosed therein, stomachs of the animals are typically examined two hours after dosing a compound. Methods for determining subchronic gastrointestinal safety are disclosed and/or referred to in the following references: Melarange, R., C. Gentry, et al., "Anti-inflammatory and Gastrointestinal Effects of Nabumetone or Its Active Metabolite, 6-Methoxy-2-naphthylacetic Acid (6MNA)", *Dig. Dis. Sci.*, Vol. 37 (1992), pp. 1847–1852; and Wong, S., S. J. Lee, et al., "Antiarthritic Profile of BF-389—A Novel Anti-inflammatory Agent With Low Ulcerogenic Liability", *Agents Actions*, Vol. 37 (1992), pp. 90–91.

Methods for determining acute gastroprotection are disclosed and/or referred to in the following reference: Playford, R. J., D. A. Versey, S. Haldane, M. R. Alison, and J. Calan, "Dose-dependent Effects of Fentanyl on Indometharin-induced Gastric Damage", *Digestion*, Vol. 49 (1991), pp. 198–203. In the method disclosed therein, female Lewis rats (130–175 g) are dosed perorally with the subject compound (40 mg/kg b.i.d.) or vehicle at 2 hours and immediately before administration of a gastric damaging dose of indomethacin. The rats are sacrificed 4 hours later by $CO_2$ asphyxiation. Gastric corpus damage (millimeters of hemorrhagic lesions) is measured by digitized imaging.

The preferred mode of administration of the subject compounds is peroral, but other known methods of administration are contemplated as well, e.g., dermatomucosally (for example, dermally, rectally and the like), and parenterally (for example, by subcutaneous injection, intramuscular injection, intraarticular injection, intravenous injection and the like). Ocular administration and inhalation are also included. Thus specific modes of administration include, without limitation, peroral, transdermal, mucosal, sublingual, intranasal, intramuscular, intravenous, intraperitoneal, subcutaneous, and topical administration.

Preferred doses of the subject compounds range from about 0.2 mg/kg to about 70 mg/kg, more preferably from about 0.5 mg/kg to about 12 mg/kg. Preferred injectable doses comprise from about 0.1 mg/kg to about 10 mg/kg of the subject compound. Preferred topical doses comprise from about 1 mg/cm$^2$ to about 200 mg/cm$^2$ of the subject compound applied to the skin surface. Preferred peroral doses comprise from about 0.5 mg/kg to about 50 mg/kg, more preferably from about 1 mg/kg to about 20 mg/kg, more preferably still from about 2 mg/kg to about 10 mg/kg, of the subject compound. Such doses are preferably administered from about once to about six times daily, more preferably from about twice to about four times daily. Such daily doses are preferably administered for at least one week, also preferably for at least two weeks, also preferably at least one month, also preferably for at least 2 months, also preferably for at least 6 months, 1 year, 2 years, or more.

The following non-limiting examples illustrate the subject invention.

EXAMPLE A

A pharmaceutical composition in tablet form is prepared by conventional methods, such as mixing and direct compaction, formulated as follows:

| Ingredient | Quantity (mg per tablet) |
| --- | --- |
| 1-(7-tert-butyl-3,3-dimethyl-2,3-dihydrobenzo[b]furan-5-yl)-pentan-1-one | 200 |
| Microcrystalline Cellulose | 100 |
| Sodium Starch Glycollate | 30 |
| Magnesium Stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

EXAMPLE B

A pharmaceutical composition in capsule form is prepared by conventional methods, formulated as follows:

| Ingredient | Quantity (mq per capsule) |
| --- | --- |
| 1-(7-tert-butyl-3,3-dimethyl-2,3-dihydrobenzo[b]furan-5-yl)-3-chloro-3-methyl-2 butan-1-one | 200 |
| Lactose | To fill to volume of capsule |

The above capsule administered orally once a day substantially reduces the symptoms of a patient afflicted with rheumatoid arthritis or osteoarthritis.

EXAMPLE C

A pharmaceutical composition in liquid form is prepared by conventional methods, formulated as follows:

| Ingredient | Quantity |
| --- | --- |
| 1-(7-tert-butyl-3,3-dimethyl-2,3-dihydrobenzo[b]furan-5-yl)-cyclopropylbutan-1-one | 200 mg |
| EtOH | 4 ml |
| Methyl cellulose | 0.4 mg |
| Distilled water | 76 ml |
| Tween 80 | 1.6 ml |

50 ml of the above composition administered perorally once a day substantially reduces the symptoms of a patient afflicted with rheumatoid arthritis or osteoarthritis.

EXAMPLE D

A pharmaceutical composition in liquid form is prepared by conventional methods, formulated as follows:

| Ingredient | Quantity |
| --- | --- |
| Microcrystalline (micronoized) 1-(7-tert-butyl-3,3-dimethyl-2,3-dihydrobenzo[b]furan-5-yl)-ethan-1-one | 200 mg |
| Avicel (microcrystalline cellulose) | 50 mg |
| Tween 80 | 1.6 ml |
| Methyl cellulose | 0.4 mg |
| Deionized water | 80 ml |

100 ml of the above composition administered perorally twice a day substantially reduces the symptoms of a patient afflicted with rheumatoid arthritis or osteoarthritis.

EXAMPLE E

An oral solid pharmaceutical composition is prepared by conventional methods, formulated as follows:

| Ingredient | Quantity (% by weight) |
| --- | --- |
| 1-(7-tert-Butyl-3,3-dimethyl-2,3-dihydrobenzo[b]furan-5-yl)-4-cyclopropylbutan-1-one | 20 |
| Pluronic F108 | 40 |
| Tween 80 | 40 |

EXAMPLE F

An oral solid pharmaceutical composition is prepared by conventional methods, formulated as follows:

| Ingredient | Quantity (% by weight) |
| --- | --- |
| 1-(7-tert-Butyl-3,3-dimethyl-2,3-dihydrobenzo[b]furan-5-yl)-4-cyclopropylbutan-1-one | 50 |
| Triglycerides and derivatives | 45 |
| Cremaphor EL | 5 |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

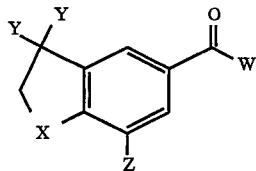

wherein
(a) X is oxygen;
(b) each Y is independently hydrogen or unsubstituted straight, branched or cyclic alkanyl having from 1 to about 3 carbon atoms, or the two Y's are bonded to form an alkanyl ring having from 3 to about 7 carbon atoms;
(c) Z is hydrogen or unsubstituted branched or cyclic alkyl, or unsubstituted or alkanyl-substituted phenyl, said alkyl having from 3 to about 10 atoms other than hydrogen; and
(d) W is straight, or branched alkyl, unsubstituted or substituted, saturated or mono- or di-unsaturated with double bonds except that no terminal carbon atom is part of a double bond; substituted or unsubstituted cycloalkyl; substituted or unsubstituted aryl; W having from 1 to about 15 atoms other than hydrogen;

where when both Y are hydrogen, Z is not hydrogen.

2. The compound of claim 1 wherein each Y is independently selected from the group consisting of hydrogen, methyl and ethyl; and Z is selected from the group consisting of hydrogen, unsubstituted $C_4$–$C_6$ branched alkanyl having 2 branches, unsubstituted $C_4$–$C_6$ cycloalkanyl, and unsubstituted phenyl.

3. The compound of claim 2 wherein both Y are methyl, and Z is selected from the hydrogen or t-butyl.

4. The compound of claim 3 wherein Z is t-butyl.

5. The compound of claim 2 wherein W is $C_1$–$C_6$ straight or single-branched alkyl, saturated or unsaturated with one double bond between non-terminal carbon atoms, or $C_3$–$C_6$ cycloalkanyl or aryl, unsubstituted or monosubstituted with a substituent selected from the group consisting of halo, hydroxy, thiol, phenyl, heteroaryl and heterocycle; W having from 1 to about 7 atoms other than hydrogen.

6. The compound of claim 5 wherein both Y are methyl, and Z is t-butyl.

7. The compound of claim 5 wherein the alkyl of W is substituted with one or more heteratom selected from the group consisting of oxygen, sulfur, nitrogen or combinations thereof.

8. The compound of claim 2 wherein W is $C_1$–$C_4$ straight or single-branched alkyl, saturated or unsaturated with one double bond between the carbon atom bonded to the carbonyl carbon atom and an adjacent non-terminal carbon atom, unsubstituted or monosubstituted with a substituent selected from the group consisting of chloro, bromo, and hydroxy; or unsubstituted $C_3$–$C_6$ cycloalkanyl.

9. The compound of claim 8 wherein both Y are methyl, and Z is t-butyl.

10. The compound of claim 2 wherein W is selected from the group consisting of methyl, ethyl, n-propyl, n-butyl, i-propyl, cyclopropyl, cyclopentyl, 3-cyclopropylpropyl, 2-chloro-2-methylpropyl, 2-hydroxy-2-methylpropyl, 2-methyl-1-propenyl, 2-thiabutyl, 2-thiapropyl, 2-sulfinylpropyl, and aceylthiomethyl.

11. The compound of claim 10 wherein both Y are methyl and Z is t-butyl.

12. The compound of claim 11 wherein W is 3-cyclopropylpropyl.

13. The compound of any of claims 5, 8, and 10 wherein both Y are hydrogen.

14. A composition comprising a compound of any of claims 1, 5, 9, and 12 and a pharmaceutically-acceptable carrier.

15. A method of treating inflammation or pain comprising administration, to a human or lower animal in need of such treatment, of a safe and effective amount of a compound of any of claims 1, 5, 11, and 12.

16. A method of treating arthritis comprising daily peroral administration, to a human in need of such treatment, of from about 1 mg/kg to about 20 mg/kg of a compound of any of claims 1, 5, 11, and 12.

* * * * *